United States Patent
Shih

(10) Patent No.: US 9,757,271 B2
(45) Date of Patent: Sep. 12, 2017

(54) HEMOSTASIS WOUND HEALING DEVICE FOR DYNAMIC ELASTIC INJURY SITE

(71) Applicant: Lih-Bin Shih, San Diego, CA (US)

(72) Inventor: Lih-Bin Shih, San Diego, CA (US)

( * ) Notice: Subject to any disclaimer, the term of this patent is extended or adjusted under 35 U.S.C. 154(b) by 226 days.

(21) Appl. No.: 14/388,256

(22) PCT Filed: May 27, 2013

(86) PCT No.: PCT/US2013/042785
§ 371 (c)(1),
(2) Date: Sep. 26, 2014

(87) PCT Pub. No.: WO2013/181118
PCT Pub. Date: Dec. 5, 2013

(65) Prior Publication Data
US 2015/0073326 A1    Mar. 12, 2015

Related U.S. Application Data

(60) Provisional application No. 61/689,073, filed on May 29, 2012.

(51) Int. Cl.
*A61F 13/00*        (2006.01)
*A61F 7/00*         (2006.01)
(Continued)

(52) U.S. Cl.
CPC .............. *A61F 7/0085* (2013.01); *A61F 7/02* (2013.01); *A61F 7/10* (2013.01);
(Continued)

(58) Field of Classification Search
CPC .... A61F 13/02; A61F 7/02; A61F 7/10; A61F 7/00; A61F 13/00; A61F 2013/0028;
(Continued)

(56) References Cited

U.S. PATENT DOCUMENTS 3,754,549 A    8/1973   Nelkin
3,780,537 A    12/1973  Spencer
(Continued)

FOREIGN PATENT DOCUMENTS

WO    WO 01-39704 A1    6/2001
WO    WO 2004-043695    5/2004

OTHER PUBLICATIONS

Walker et al. Comparison of the FemoStop device and manual pressure in reducing groin puncture site complications following coronary angioplasty and coronary stent placement. Int J Nurs Pract. Dec. 7(6): 366-375.

(Continued)

*Primary Examiner* — Ophelia A Hawthorne

(57) ABSTRACT

A topical cooling compressive hemostasis wound healing device and methods thereof for affecting a percutaneous access site wound or an acute surgical wound. The device delivers and transports cooling to affect and control vasculature and musculoskeletal motions surrounding the injury site during the blood coagulation, hemostasis, and wound healing phases. The device has a viscoelastic and thermally conductive surface to deliver and transport an adjustable compressive pressure to resist outward blood flow, thus improving patient safety and clinical outcomes. The device is anatomically conforming and treats not only the specific injury site, but also its surrounding anatomical structures together as means to prevent unpredictable delayed hemostasis breach. The device provides comfort to the patient by allowing mobility upon wound healing, thus reducing back pain and strain resulting from being in a constrained position for a prolonged period of time which is known to cause additional medical events. The device reduces pain, inflammation, swelling, and scar formation on the injury site of a (Continued)

patient and promotes hemostasis, sustains hemostasis, and improves overall wound healing quality.

21 Claims, 9 Drawing Sheets

(51) Int. Cl.
A61F 7/02 (2006.01)
A61F 7/10 (2006.01)
(52) U.S. Cl.
CPC ............... *A61F 13/00063* (2013.01); *A61F 2007/0054* (2013.01); *A61F 2007/0228* (2013.01); *A61F 2007/0231* (2013.01); *A61F 2007/0247* (2013.01); *A61F 2007/0261* (2013.01); *A61F 2007/0292* (2013.01); *A61F 2013/0028* (2013.01)
(58) Field of Classification Search
CPC ...... A61F 2007/0292; A61F 2007/0261; A61F 2007/0247; A61F 2007/0231; A61F 2007/0228; A61F 2007/0054; A61F 13/00063; A61F 7/0085; B32B 7/02; B32B 27/08; C09K 5/06
See application file for complete search history.

(56) References Cited

U.S. PATENT DOCUMENTS

| | | | |
|---|---|---|---|
| 4,957,105 A | | 9/1990 | Kurth |
| 5,792,173 A | | 8/1998 | Breen et al. |
| 5,968,072 A | * | 10/1999 | Hite ............... A61B 17/1325 606/202 |
| 5,997,564 A | | 12/1999 | Shehata et al. |
| 2003/0028214 A1 | | 2/2003 | Benz et al. |
| 2004/0176796 A1 | | 9/2004 | Akerfeldt et al. |
| 2006/0079823 A1 | * | 4/2006 | Utterberg ............ A61F 13/0246 602/53 |
| 2006/0095073 A1 | | 5/2006 | Beto et al. |
| 2006/0229664 A1 | | 10/2006 | Finkielsztein et al. |
| 2007/0130840 A1 | | 6/2007 | Jouhannet |
| 2007/0161932 A1 | | 7/2007 | Pick et al. |
| 2008/0015665 A1 | | 1/2008 | Lachenbruch |
| 2008/0249447 A1 | | 10/2008 | Brown et al. |
| 2009/0005718 A1 | * | 1/2009 | Lightbourne ......... A61F 5/0111 602/75 |

OTHER PUBLICATIONS

Kang et al. A Retrospective Review on Feasibility and Safety of a New Pneumatic Compression Device for Femoral Arteriotomy Hemostasis, Kr J. Radiol. Jan.-Feb. 2012;13(1):61-65.

King et al. A randomized controlled trial assessing the use of compression versus vasoconstriction in the treatment of femoral hematoma occurring after percutaneous coronary intervention, Heart & Lung, 2008;37:205-210.

* cited by examiner

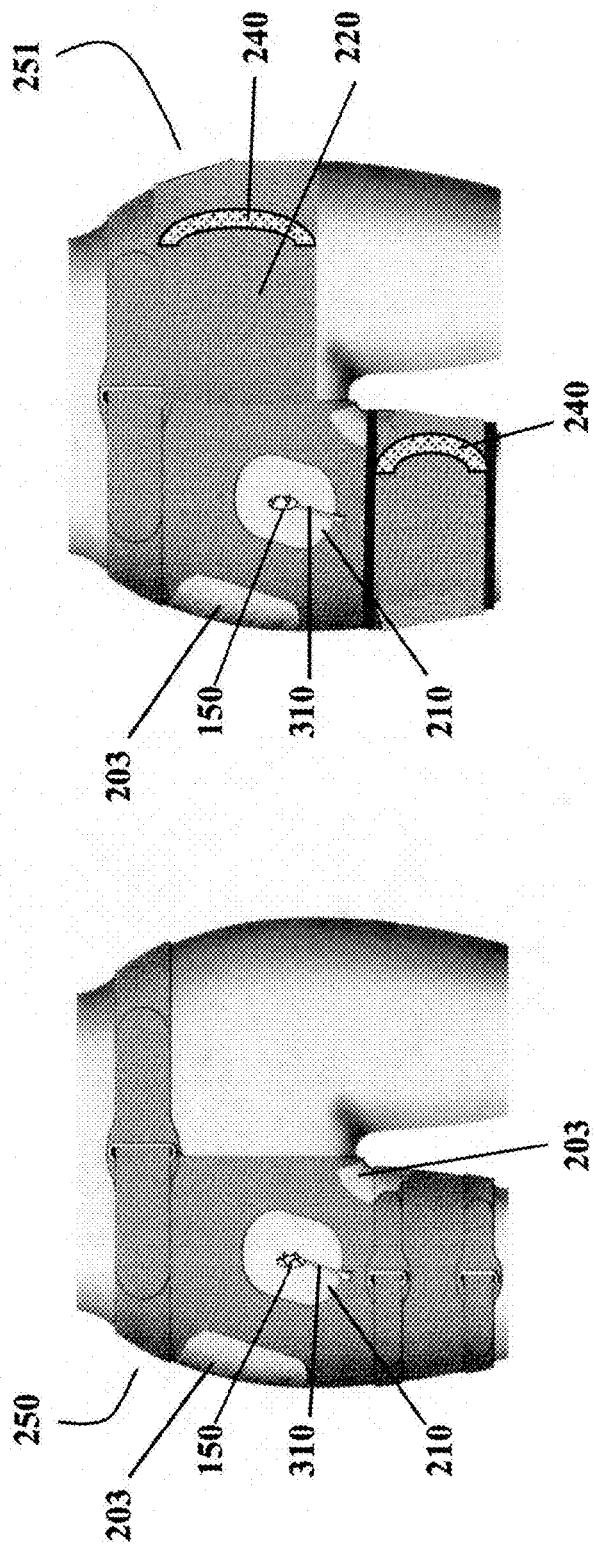

HEMOSTASIS WOUND HEALING DEVICE FOR DYNAMIC ELASTIC INJURY SITE

CROSS-REFERENCE TO RELATED APPLICATION

This application claims priority to U.S. Provisional Application No. 61/689,073, filed on May 29, 2012, which is incorporated herein by reference in its entirety.

TECHNICAL FIELD

This concept generally concerns hemostasis wound healing devices for a dynamic and elastic vascular injury microenvironment, and more particularly to an anatomically conforming topical cooling compressive device and associated methods for hemostasis and wound healing of percutaneous access site and acute surgical wounds.

BACKGROUND ART

Human physiological signals are perpetual. These signals are spontaneous or induced with molecular, cellular chemical, and/or neural origins. Many of these physiological signals manifest themselves in motions in order to perform biologic and biochemical functions that sustain life. The better known motions are heartbeats, respiration, and cardiopulmonary functions. But there are far subtler motions in all parts of a human body necessary and essential to support life. These physiological motions have been shown to follow certain non-linear dynamic laws and possess fractal features and entrainment properties. These physiological motions are related to demographic factors, for example, gender and age, and closely associated with the health or disease conditions of a human body. Physiological dynamics, while not always seen or felt by humans, are nonetheless always present and essential to life.

In particular, these constant physiological motions are present in the entire cardiovascular and circulatory system including arteries, veins, and capillaries. Vasculature motions include vasomotion, vasodilation, vasoconstriction, and vasospasm. These spontaneous motions in the vasculature system also lead to rhythmic changes in vessel diameter, wall thickness, and vessel distensibility. Furthermore, blood vessels are elastic and characterized by certain viscoelastic properties. The dynamic and elastic nature of the vessels has particular effects on the success or failure of a therapeutic cardiovascular device.

Percutaneous access for various cardiovascular interventions is considered a safer and less invasive alternative to surgery. This procedure was developed in early 1950's and has since evolved into a popular and useful procedure treating a wide range of cardiovascular and vascular diseases including abdominal aortic aneurysm and heart valve repairs. Percutaneous access is either diagnostic or interventional (for example, percutaneous coronary intervention or PCI) with several possible access sites including access through an artery or a vein (for example, femoral, radial, or brachial), or transapical access. Each access site has its advantages and limitations. The choice of the access site is dependent on the disease condition and certain relevant clinical factors. But the choice can also be the preference of a practicing interventional cardiologist or radiologist. In all of these percutaneous interventions, there is a common denominator, that is, hemostasis and healing of the vascular wound.

The access site preference in percutaneous procedures has evolved over time and is currently geographically stratified. Today, the angioplasty procedure in the US is >95% transfemoral while transradial access is favored in Europe and Asia at approximately 70%. In the US, there has been a surge of radial access since 2007, mainly in response to the unabated bleeding and medical complications associated with the transfemoral access. Reducing femoral bleeding complications is cited as the sole reason for converting to radial access, even though radial access has its own limitations and disadvantages. Despite unabated bleeding medical events, femoral access is unlikely to be fully replaced because of its certain clinical advantages. Successful access site hemostasis and subsequent wound healing is important by itself as bleeding complications are associated not only with serious human costs including fatality, amputation, life-long pain, and disability, but also with significant healthcare expenditures in managing bleeding complications. Proper hemostasis and healing of the access site wound is an integral component to the underlying intervention, as it either contributes to the success of, or compromises, the intervention.

Traditional designs of hemostasis devices for percutaneous access site are based on the mechanistic barrier concept of treating the "hole" of the injured vessel more like a hole in a leaking water pipe, that is, a leaking water pipe which is rigid and stationary with constant dimensions. This barrier concept is reflected by many conventional terms such as "seal", "plug", or "clamping". As a means to cause hemostasis, the implant device provides a physical barrier to "plug" or "seal" a vascular "hole", while the current topical devices provide a mechanical barrier to "clamp" an injured vessel to stop outward blood flow. In reality, these sealing and clamping actions only provide a resistive force to resist blood, particularly resisting high velocity arterial blood from gushing out upon sheath removal. These actions do not cause hemostasis as defined by the completion of a cascade of time-dependent cellular processes of platelet aggregation, fibrin matrix formation, and subsequent wound healing phases. Moreover, blood vessels are not a rigid stationary structure. Instead, blood vessels are soft, elastic, and in various modes of perpetual motions and constantly changing vessel diameter, wall thickness, and tone.

The nature of the dynamic and elastic injury site explains why a precisely fitted implant may be disoriented or dislocated after seemingly initial hemostasis success and why precise topical clamping can still cause bleeding to turn internal or cause hematoma to form outside of the access location. The concept of plugging or clamping a "hole" in a rigid and stationary structure is not applicable to human vessel systems. Furthermore, an injury in a human body, even if local or perceived as local, is far from being localized, and is connected to and affected by, and also affects, the surrounding anatomical structures in both known and unknown manners. Managing the injured vessel "hole" must take a broader view beyond the injury site. In addition, the anatomy and the surrounding vascular and musculoskeletal structures at the femoral site are far more complex and significantly different from that at the radial site. But the current barrier concept does not differentiate between the two and rely on the same clamping mechanism to clamp the "same (radial or femoral) hole" of an injured vessel.

It is well documented that the initial seemingly successful hemostasis on the skin puncture surface can turn into a serious bleeding medical event later in an unpredictable way. The timeframe for delayed hemostasis breach is from hours to days, and in rare cases, months. And it can manifest in several forms including life-threatening "invisible" retroperitoneal bleeding or hematoma formed at location(s) other than the access site. These well-known clinical observations signify that the bleeding direction is not limited to the skin puncture surface as commonly perceived, and further validate that the "hole" is not a stationary structure. To date, there have been no effective answers to these clinical observations, nor an effective way to predict, thus prevent, delayed hemostasis breach.

There are two types of topical hemostasis devices currently on the market to manage bleeding at the access site. One is a "topical patch", applied over the skin puncture site where the manufacturer claims to stop bleeding faster by visually judging no blood oozing out on the skin puncture surface. The other is the equivalent of manual compression, that is, by providing a compression force with a mechanical device. The former (topical patch) provides a false sense of hemostasis as the injury is the breached vessel under the skin and the skin surface hemostasis is not an indication of true and sustainable hemostasis. Nor does the latter (manual or device compression) solve the problem. In fact, an exhaustive scientific literature search has shown that compression pressure either at the vascular level, or at the skin level, does not cause platelet aggregation and fibrin formation. Furthermore, a strong and prolonged compression is known to hinder cellular coagulation and cause additional injury and neurological damage to the patient.

By relying on the barrier concept, access site bleeding complications, particularly at the anatomically more complex femoral site, remain unabated after more than half a century. In the meantime, advances in percutaneous technique have led to more complex interventions requiring larger catheter size (for example, 24 F in certain interventions) and more aggressive use of anticoagulants, both of which are known risk factors of bleeding complications. In spite of significant evolutions in percutaneous techniques, manual compression remains today the "gold standard" in managing access site hemostasis, even though ample clinical experiences and large scale statistics have confirmed that manual compression is inadequate and inapplicable in many situations. Today, access site bleeding and vascular complications remain a significant medical and economic issue decades after the advent of the percutaneous procedure. A safe and rigorous clinical solution to manage access site bleeding would improve patient safety and contribute to advancing the percutaneous technique.

DISCLOSURE OF INVENTION

Recognition that the dynamic and elastic nature of the injured vessel plays a key role in affecting and sustaining hemostasis in the vascular wound and in surgical wound is an aspect of embodiments of this invention. The present concept teaches that, while a barrier to stop blood from gushing out is immediately needed upon completing the medical procedure, it is not enough to sustain hemostasis or to ensure patient safety. Furthermore, as demonstrated in literature, certain hemostasis management methods may turn harmful causing additional harm to a patient. Included also is how to timely affect and control the injured vessel during the initial critical platelet aggregation and fibrin formation phases to allow the fibrin clot to attain strength to sustain hemostasis.

Embodiments of the invention disclose a design to apply appropriate compressive force without interfering with cellular hemostasis processes or compromise wound healing. Included is a cooling element which provides an initial cooling profile on the injured skin surface to cause vasoconstriction and hemostasis, and a follow-on cooling profile to stabilize the injured vasculature structure and promote hemostasis, sustain hemostasis, and improve wound healing quality. Included further is a lateral stabilization device to stabilize and apply mild lateral compression to the surrounding vascular and musculoskeletal structures of the injury site as means to promote and sustain hemostasis. Included also is the design of a topical hemostasis wound healing device which is configured to the specific anatomical features of the injury site. Studies have shown that a patient in a strained uncomfortable position for an extended period of time following medical intervention is more likely to develop delayed bleeding and/or hematoma event. Embodiments of this invention disclose how to provide certain mobility to the patient upon wound healing and without requiring the patient to be immobilized or constrained in a rigid and strained position for a prolonged period of time.

Embodiments of the invention also provide effective and appropriate compressional pressure to resist outward blood flow, and appropriate cooling at the injury site to control and affect vasculature motions at the injury site and at the surrounding vascular and musculoskeletal structures. The device is anatomically conforming and comfortable to a patient during hemostasis and recovery wound healing phases. The device allow a patient to rest, and yet does not require a patient to be completely immobilized during the entire compression period, typically from six hours up to overnight. The device allows a patient to gain gradual mobility as the wound heals. Such gradual increase in mobility includes, but is not limited to, tilting the upper body to eat or to perform bathroom functions. The device, unlike the current compression devices, does not place a patient in a prolonged strained position to cause back pain and further exacerbate the injury. The device is comfortable to a patient to use while providing anesthetic and analgesic effects to a patient. The device accelerates hemostasis, promotes re-epithelialization, sustains hemostasis, reduces scar formation, reduces inflammation, reduces swelling, reduces pain, and improves overall wound healing quality. In sum, this new concept provides solutions to reduce bleeding complications and achieve better clinical outcomes in percutaneous interventions and in surgical interventions.

Embodiments of the present invention provide for a device and method configured to the anatomy of the injury site and configured to the surrounding vascular and musculoskeletal structures of the injury site. It provides for a device and method that allows a patient with mobility upon wound healing, without having to be constrained to a strained position for a prolonged period of time. It also provides for a device that minimizes the manipulations of a patient by attending medical personnel while providing post-intervention care. Embodiments of the invention provide for a device and method that affect and control the physiological dynamic and elastic injury microenvironment of a patient to promote timely platelet aggregation, fibrin formation, blood coagulation, and to sustain hemostasis, accelerate re-epithelialization, and promote wound healing, wherein wound healing includes a hemostasis phase, an inflammation phase, a proliferation phase, a remodeling phase, and a maturation phase, or any combination thereof. Also provided are analgesic and anesthetic effect on a patient to reduce pain, reduce inflammation, reduce swelling, reduce scar formation, and reduce potentials for infection.

In one aspect of the invention, the hemostasis wound healing device (HWHD) consists of two components: one component to provide lateral stabilization of the injury site, or the vasculature and musculoskeletal structures surrounding the injury site, or both, and one component to provide cooling and compression to the injury site and its immediate anatomical vicinity. In one aspect of the invention, the first component is a Lateral Stabilization Garment (LSG) and the second component a Cooling Pad (CP) or a Compressive Cooling Device (CCD), or both. In one aspect of the invention, each of these two components and its sub-components can be used individually. In one aspect of the invention, any one component or its subcomponents of the HWHD can be used in combination with one another and together to provide therapy.

In one aspect of the invention, the LSG is configured so that it is placed, in flat and continuous configuration, under a patient prior to medical intervention. In one aspect of the invention, the injury site can be on the front of the torso of a patient, by way of example and without limitation, the heart or the abdominal, or the back of the torso, or an extremity. In one aspect of the invention, the LSG is wrapped around the injury site of a patient by an attending medical personnel after the intervention is completed. In one aspect of the invention, the LSG is configured to the anatomy of the injury site so that after the attending medical personnel grabs both ends of the LSG and secures it on top of the patient surrounding the injury site after the medical procedure, while leaving an overlap of one end to cover the other end. In one aspect of the invention, when the LSG is wrapped around an injured patient, the overlap is not excessive so as to go underneath the surrounding torso of the injury site. In one aspect of the invention, closing both ends of the LSG by an attending medical personnel is so that the attending personnel does not need to disturb, by turning or lifting, the patient or the patient's injury site, before the LSG is applied.

In one aspect of the invention, the LSG is configured so that it is substantially evenly distributed on both sides of a patient in a lying down position. In another aspect, the LSG is configured to allow an attending medical personnel to pull both ends of the LSG and reattach both ends of the LSG together over the patient to secure the LSG on the patient. In yet another aspect, the LSG covers the injury site and the surrounding areas of the injury site and in another, the LSG covers only the injury site. In still another aspect of the invention, the LSG covers the surrounding anatomical structures of the injury site while leaving an open area at the injury site and expose the injury site to allow the attending personnel to apply an additional therapeutic means over the injury site. The LSG can have detachable extensions which allow the attending personnel to gain the grip to wrap the LSG around a patient and secure it without turning or disturbing the patient. The detachable extensions may be discarded after the LSG is secured over a patient.

In one aspect of the invention, the LSG comprises one or more openings to allow one end of the LSG to pull through and overlap with the other end of the LSG. The opening can be, for example, a hole, or a buckle with a single hollow center. The shape of the hole or of the hollow center of the buckle can be substantially rectangular or substantially round or substantially oblong or substantially oval. According to embodiments of the invention, after the medical intervention is completed, an attending medical personnel can bring both ends of the LSG over a patient's injury site by inserting one end of the LSG through the hole or the hollow center of the buckle, and then pulling two ends, one hand on each end, in opposite directions in substantially equal force to secure the LSG over the patient.

In one aspect of the invention, the mechanism of securing the LSG over the patient is by pulling two ends of the LSG in opposite directions to allow the application of lateral compression over the injury site and its surrounding anatomical structures. One end of the LSG can be secured to the other end of the LSG by various means such as a hook-and-loop fastener, for example, Velcro®, an adhesive, an adhesive tape, a harness, a buckle, a clasp, a hook, a loop, a safety pin, a D-ring, or the like, or any combination thereof. The application of the lateral compressive force can be adjusted by the degree of pulling by the attending personnel. The application of the lateral compressive force allows the vascular wound, skin wound, or surgical wound to return to its anatomical configuration facilitating hemostasis and wound healing.

In one aspect of the invention, the LSG serves to stabilize a patient's injury site or the surrounding anatomical structures of the injury site, or both. The LSG further serves as an anchor to allow the application of additional topical therapeutic devices to the injury site without having the additional topical device to come in direct contact with the intact skin. In other words, the additional topical devices can be secured to a patient by securing to the LSG, but not to the patient's skin via adhesive tapes, a clamp, or other devices.

In one aspect of the invention, the LSG is made of transparent polymeric materials to provide transparency for visual inspection by attending medical personnel. The LSG can be made of fabric to provide comfort to a patient, and it can be stretchable. It is contemplated that the LSG fabric material is capable of stretching in the securing direction between about 5% (or 105% of original in width direction) and about 500% (or 5 times of the original width).

The LSG can be configured to various types of surgical incisions at various parts of a human body, and to various types of percutaneous procedures at different anatomical sites, for example, radial access, femoral access, brachial access, hemodialysis access, transapical access, and the like. In one aspect of the invention, the present LSG apparatus is configured for transfemoral application and provides for the stabilization and lateral compression of the lower torso right above the femoral access site, of the anatomical structure along the oblique inguinal ligament direction extending out from the femoral access site, and of the upper portion of the leg right below the femoral access site. The upper part of the LSG is configured to the anatomy of the lower torso, the middle part of the LSG is configured to the anatomy of the inguinal ligament direction, and the lower part of the LSG is configured to the anatomy of the upper portion of the leg right below the access site.

In one form, the flat continuous LSG is placed under a patient prior to transfemoral intervention and, after the procedure is completed, an attending medical personnel grabs both ends of the LSG, with or without a detachable extension, and wrap them around the front side at a substantially center location of the patient. The attending personnel can provide mild compressional force by pulling tight and securing the LSG at the front side of the patient.

The LSG for femoral access site application may be a continuous structure without any opening on the front side, and is applied to a patient after another hemostasis device, either an implant or a topical device, is applied to the patient. The LSG for femoral access site application may also have an opening to expose the injury site. The shape of such opening can be substantially round, or substantially rectangular, or substantially square, or substantially oblong, or substantially oval. The shape of the opening in the LSG for femoral access site application can be any of the above or of an irregular shape. In one aspect of the invention, the opening in the LSG has the approximate surface area between about 6 cm$^2$ and about 60 cm$^2$. The LSG can be, after intervention, wrapped around the front side of a patient with the sheath still unpulled and inside the access site of the patient and situated in the LSG opening.

In one aspect of the invention, the HWHD comprises a second component to provide cooling and compression to the injury site and its immediate anatomical vicinity, that is, a cooling pad (CP). The CP may contain a coolant imparting cooling to a patient in a prescribed manner. The CP can provide cooling to the injury site and to the surrounding vascular and musculoskeletal structures. The CP can provide compressive force to the injury site to resist blood outward flow upon sheath removal and stabilize the injury site and the vascular segments proximal to the injury site. The CP further quenches, minimizes, and reduces vascular and musculoskeletal movements of the injury site, and of the connected anatomical structures during the critical initial phases of platelet aggregation and fibrin clot formation.

In one embodiment of the invention, the CP is shaped and sized to be larger than the opening of the LSG. The CP can be a solid piece with a continuous surface without an opening. In one aspect of the invention the CP covers the injury site and its surrounding anatomical structures by securing the CP on the intact skin surface with biocompatible adhesives and the like. The CP can cover the injury site which is already covered by a sterilized gauze or the like. In one aspect of the invention, the CP has an opening centered around and surrounding the injury site, thus providing cooling only to the surrounding anatomical structures of the injury site.

In an embodiment of the invention, the CP is secured by attaching to the LSG with attachment devices including but not limited to, a hook-and-loop fastener (for example, Velcro®), an adhesive, an adhesive tape, a harness arrangement, a buckle, a clasp, a hook, a loop, a safety pin, a D-ring, or the like. The CP can be made of a polymeric material. The outer surface of the CP, which is exposed to the ambient conditions, can be made of thermal insulating polymeric materials to prevent heat loss (or cooling loss, in this case) to the ambience. The thermal insulating material can be, but is not limited to, neoprene, polyurethane rubber, silicone rubber, foams, or the like. The inner surface of the CP, which can be in direct contact with the intact or the injured skin or can be in direct contact with a sterilized gauze which in turn in direct contact with the intact or the injured skin, may be made of thermal conductive materials to impart cooling to the injury site and its surrounding structures. In another embodiment, the inner surface of the CP is made of soft fabric materials comfortable to human skins.

In one aspect of the invention, the second component of HWHD providing cooling and compression comprises a Compressive Cooling Device (CCD). The CCD may further comprise a Cooling Compressive Compartment (CCC) and a Cooling Compressive Surface (CCS). The CCC may comprise a coolant container and a vertical displacement casing and the CCS may comprise a rigid component and an elastic component. In one aspect of the invention, the CCS is integrated into one side of the CCC during fabrication, that is, the side facing the wound. In an aspect of the invention, the CCS is post-fabricated onto one side of the CCC, that is, the side facing the wound. The coolant container in the CCC can be configured to provide vertical displacement as one unit with the vertical displacement casing. In another aspect, the coolant container in the CCC performs vertical displacement independent of the vertical displacement casing, that is, the coolant container performs vertical displacement by moving up and down relative to the vertical displacement casing, and the casing does not move with the coolant container.

In an embodiment, the CCD delivers a compressive force, through the vertical displacement of the CCC, to the wound site to resist blood from gushing out upon sheath removal or upon the completion of surgical intervention. The CCD can have a rigid component to resist blood outward flow. The CCD can have a soft and viscoelastic component providing a soft surface in direct contact with the breached injured skin and the vessel wound to improve comfort and safety for the patient, thus reducing medical complications. The CCS may be thermally conductive. The CCS can be configured to deliver and transport temperature from the CCC to the wound site and remove heat from the wound site.

In one aspect of the invention, the surface area of the CCS is of the same surface area as the breached skin injury. For example, if the interventional catheter is 8 F, the breached skin has an injury site of 0.27 cm in diameter, the breached skin surface area is 0.056 cm$^2$, and the CCS has a surface area of 0.056 cm$^2$. The CCS may be formed to have a surface area between the size of the breached skin surface area and 500 times (500×) the size of the breached skin surface area. In this example, the CCS surface area for an 8 F catheter injury site can be 28 cm$^2$ (about 500 times of the injury surface area). Another alternative is for the topical CCS surface area to be 1,000 times or greater of the injured skin breached surface area, depending on medical needs.

The CCS surface area can be of various shapes and geometries. For example, the compressive surface area of 50 cm$^2$ can be substantially square with approximately 7 cm on each side, or substantially rectangular with approximately 5 cm on one side and approximately 9 cm on the other side, or substantially circular with an 8 cm diameter. The larger CCS surface area than the injury site is to provide more even compressive pressure so as to affect hemostasis and wound healing without causing additional vessel injury or prolonged tourniquet effect which often lead to medical complications. The larger CCS surface area is to heal the vicinity of the wound affected by percutaneous access or by surgery. The CCS can be configured so that the breached skin is at the center of the CCS or it can be configured so that the breached skin is off the center of the CCS.

In one aspect of the invention, the CCS can be formed with a raised ridge where the raised ridge is centered around the breached skin. Further, the CCS can have a substantially conical surface with low radius of curvature, that is, a convex shape with the protruding part facing the wound. The CCS can have a raised ridge substantially centered at the breached injured skin surface. The raised ridge in the CCS can be off the center of the wound. In one aspect of the invention, the CCS has a raised ridge along the longitudinal direction of the injured vessel under the skin. The CCS can be formed with a flat surface, and it can be configured and conformed to the anatomy of the wound site and to the surrounding anatomical structures of the wound site.

In one aspect of the invention, the surface of the CCS can be formed as a square or substantially square, a rectangle or substantially rectangle, a square with a rounded edge, a rectangle with a rounded edge, a circle, an oblong-shape, or a substantially oblong-shaped, an irregularly-shaped area, or the like. The CCS can be in direct contact with injured skin or the injured skin can be covered with sterilized gauze or with another wound dressing, or the like, and the CCS is applied on top of the sterilized gauze or the other wound dressing.

In an embodiment the CCS is soft and has a viscoelastic characteristic to provide a soft contact with the injured skin. The CCS can be made of one material, or it can be made of at least two layers with different materials, whereas the layer away from the breached skin is a rigid material to resist blood flow while the layer on the breached skin side, or in contact with the breached skin, is soft with a low tensile modulus and a low Young's modulus. The CCS can be a material that has both the required rigidity to resist blood flow and the required softness to provide comfort and safety to the patient. The soft component of the CCS can be an elastomer with a tensile modulus from 50 kPa to 100 MPa. As a reference, typical human skin has the tensile strength at approximately 20 MPa and typical human vessels have the tensile strength of between 50 kPa and 3.0 MPa.

The CCS may be thermally conductive. Thermal conductivity and heat exchange properties act to conduct cooling from the CCC to the wound site and to dissipate heat from the wound site. The thermal conductive material may be a polymer, for example and without limitation, a plastic, a natural rubber, a synthetic rubber, an elastomer, a composite, a compounded material, a blend, or a combination thereof. The thermal conductive polymer can have a thermal conductivity between about 0.15 W/(m-K) and about 100 W/(m-K), where W/(m-K) is watts per meter Kelvin. The thermal conductive material may be a metal or an alloy, known for good thermal conductivity. In one aspect of the invention, the thermally conductive material in the CCS is selected from a group of proprietary-engineered plastic or elastomers whereas the thermal conductivity is between about 0.15 W/(m-K) and about 100 W/(m-K).

In one embodiment of the invention, the CCS incorporates a therapeutic agent, and delivers and transports a therapeutic agent to the breached injured skin to affect and control vasculature motions during hemostasis, thus to sustain hemostasis and improve wound healing quality. The therapeutic agent can be selected from the group consisting of a neural blockade agent, an anti-inflammatory agent, an anesthetic agent, an analgesic agent, a pain killing agent, a vasoconstriction agent, a sclerosant agent, and any combination thereof.

The rigid material of the CCS resists blood outward flow. The rigid material of the CCS can be a metal or an alloy, it can be a polymer, such as, a plastic, a natural rubber, a synthetic rubber, an elastomer, a composite, a compounded material, a blend, or a combination thereof. The rigid component of the CCS provides compressive pressure between about 0.2 psi (pounds per square inch) to about 20 psi. As a reference, a typical human arterial blood pressure of 180 mmHg is 3.5 psi.

The soft and viscoelastic component of the CCS over the breached injured skin providing comfort and safety to the patient is selected from the class of natural rubber, synthetic rubber, silicone rubber, or other elastomers and the like. The soft and viscoelastic component of the CCS has the tensile strength between about 50 kPa and about 100 MPa.

Both the rigid and the soft material of the CCS can be fabricated together to attain the desired properties of resisting blood flow, providing soft contact with the injury site, providing thermal conductivity, and delivering a therapeutic agent. The rigid and the soft materials can be two separate materials, or one single material, or one composite material that meets the application requirements. The rigid material may be configured as part of the coolant container in the CCC. The CCS can be post-fabricated onto the CCC. The material of the CCS can be transparent or semi-transparent to enable medical personnel to conduct visual inspection of the wound without disturbing the wound, or without removing the device.

In one aspect of the invention, the CCC comprises a coolant container and a vertical displacement casing. The coolant container contains a coolant at the temperature lower than the body temperature. The coolant can be contained inside the coolant container and in direct contact with the container. Alternatively, the coolant is contained inside a thin film and the thin film containing the coolant is then placed inside the coolant container. In one aspect of the invention, the coolant container containing coolant is situated above the wound site and provides cooling to the wound. The coolant dissipates cooling to the wound site in a passive manner, or the coolant dissipates cooling to the breached injury skin site by active means, for example, by electrical refrigerative force to maintain the desired cold temperature range.

The vertical displacement casing engages the coolant container and provides vertical displacement mechanism to the coolant container, and the vertical displacement of the coolant container delivers and transports compressive pressure to the wound site and its anatomical vicinity. The coolant container and the vertical displacement casing may perform vertical displacement as one unit. Alternatively, the coolant container can perform vertical displacement independent of the vertical displacement casing. In other words, the coolant container performs vertical displacement by moving up and down relative to the vertical displacement casing and the vertical movement causes the coolant container to move toward or away from the wound site The CCC material can be a metal, or a metal alloy. Alternatively, the CCC material is a polymer, such as, for example, a plastic, a natural rubber, a synthetic rubber, an elastomer, a composite, a compounded material, a blend, or a combination thereof. Further, the CCC material may comprise one or more of the following materials: a metal, a plastic, an elastomer, a fabric, a non-woven, or a combination thereof.

In one aspect of the invention, the CCC material is selected to provide thermal conductivity on the side of the CCS over the breached injury skin side, and to provide thermal insulation on all other sides, that is, outside of the CCS side to avoid heat loss, where "heat loss" means, in this application, the loss of coolant capacity to the ambience. The material of CCC is transparent or semi-transparent to enable medical personnel to conduct visual inspection of the wound without disturbing the wound, or without removing the device.

In one embodiment, the coolant container is substantially spherical, or substantially cylindrical, or substantially square, or substantially rectangular, or substantially cubical, or irregularly shaped, or the like. The coolant container may be a closed structure and the liquid coolant is injected into the container with a syringe type of instrument. In another aspect of the invention, the coolant container is with one side open and the coolant, either in a liquid or in a solid form, is either already-contained in a thin-film pouch, or is directly placed onto the container before the top cap is placed and the container is sealed afterward.

In one aspect of the invention, the thin film pouch is a polymer, which may be, for example, a plastic, a natural rubber, a synthetic rubber, an elastomer, a composite, a compounded material, a blend, or a combination thereof. The thin film may be flexible. The thin film may be chemical and corrosion resistant.

In one aspect of the invention, the coolant container has a flat surface on the wound site. The coolant container may have a soft conforming surface on the wound site and may be configured to the anatomy of the wound site and to the surrounding anatomical structures. The soft conforming surface may have a raised ridge approximately centering at the injury site, it may be conically shaped with a low radius of curvature. Further, the soft conforming surface may be thermally conductive.

In an embodiment, the coolant container is engaged to a vertical displacement casing so that the coolant container is raised from (releasing compressive pressure), or lowered to (increasing compressive pressure) the breached injured skin, and the vertical displacement of the coolant container is controlled by the casing and yet the movement of the coolant container is independent of the casing. In other words, the casing stays stationary and does not encounter vertical displacement during the application of the compressive pressure and the coolant container is moving up and down relative to the casing. The independent vertical displacement mechanism of the coolant container provides a substantially vertical-direction-only compression through vertical-movement-only of the coolant container.

The vertical-movement-only design produces no outward lateral, transverse, or twisting compressive actions on the breached injury skin, thus avoiding additional injury to the wound. Such vertical displacement of the coolant container may be precisely controlled to allow precise control of the amount of compressive force applied to the breached injured skin and the vessel wound. The vertical displacement of the coolant container may be reversible in a precise incremental manner to reduce compressive pressure at the wound site as the wound heals. The controlled partial release of compressive pressure at the wound site upon wound healing facilitates hemostasis, wound healing, and reduces pain.

In one aspect of the invention, the extent of vertical displacement of the coolant container depends on the type of injury, the anatomy of the injury site, and the anatomy of a patient including, but not limited to, patient factors such as the patient's BMI (Body Mass Index). In one aspect, the vertical displacement of the coolant container is between about 0.2 mm and up to about 10.0 cm, with the extreme high level of vertical displacement for an obese patient in femoral access site application. A typical vertical displacement is between 0.5 cm and 2.0 cm. In one aspect of the invention, the vertical displacement of the coolant container produces a compressive pressure between about 0.2 psi (pounds per square inch) to about 20 psi. As a reference, a typical human arterial blood pressure of 180 mmHg is 3.5 psi.

In an embodiment, the applied compressive pressure is initially greater (the depressed lower position of the coolant container) to resist blood flow upon sheath removal or surgery completion. The applied compression pressure can be reduced over time upon blood coagulation and wound healing. The applied compression pressure may be less (the raised higher position of the coolant container) as the coagulation process is progressed to completion and a stable fibrin clot is being formed.

In one aspect of the invention, the CCD is secured to the CP so that the CCD does not engage in lateral or any other motions, other than the vertical movement required to provide, or to release, compressive pressure to the wound. The securing mechanism to the CP can be hook-and-loop fastener, for example Velcro®, an adhesive, an adhesive tape, a harness, a buckle, a clasp, a hook, a loop, a safety pin, a D-ring, or the like, or any combinations thereof. In an embodiment, the CCD is secured to the LSG so the CCD does not engage in lateral or any other motions, outside of the vertical movement required to provide, or to release, compressive pressure to the wound. The securing mechanism to the LSG can be hook-and-loop fastener, for example Velcro®, an adhesive, an adhesive tape, a harness, a buckle, a clasp, a hook, a loop, a safety pin, a D-ring, or the like.

In an embodiment, the HWHD is applied between five minutes and eight hours, depending on the type of the injury and on hospital protocol. The HWHD may be left on the patient overnight per hospital protocol. The CCD can be exchanged every hour, or every three hours, or to the extent necessary to maintain passive cooling. The CCD may be left on the patient after the coolant has reached ambient temperature.

The coolants in the CP and the CCD can comprise different temperature profiles as a function of time, depending on medical need. Alternatively, the coolants in the CP and in the CCD can comprise the same temperature. The coolant temperature profile comprises an initial temperature profile and a follow-on temperature profile on the injured skin surface. The initial temperature profile at the breached injured skin may be between about +5° C. and about +20° C. for a duration of up to about 10 minutes. As a reference, a typical unbroken skin surface temperature in a temperature-controlled room is between 30° C. and 33° C.

In one embodiment, the follow-on temperature profile is between +10° C. to +25° C. for a duration of between about five minutes and about 20 hours. As an alternative, the follow-on temperature profile may be maintained within the range of about ±10° C. before warming to ambient temperature. The coolant container, or the CCC, or both, may be changed before, or shortly after, the follow-on temperature reaches ambient temperature. The cooling temperature profile preferably does not cause skin irritation or cold blisters.

In another aspect of the invention, the temperature in the CP, or in the CCC, or both, has more than two different temperature zones to promote cellular activity and cellular migration at the wound site, thus promoting coagulation processes and wound healing. The temperature in each zone can be altered by an active means, such as, for example, an electronically-controlled temperature device. The temperature in each zone can be altered by using a different type of coolant. The temperature of one zone can be altered depending on the temperature of other zones. Alternative, the temperature of one zone can be altered independent of the temperature of other zones, such as, for example, the temperature of a center zone is different from the temperature of the surrounding zones. The plurality of temperature zones may be selected according to the size or the nature of the wound.

In one aspect of the invention, cooling suppresses vasculature motions to provide a more stabilized microenvironment of the vascular injury site (below the skin) to allow platelet aggregation and fibrin formation to take place and to allow a fibrin clot to become stable to sustain hemostasis. Further, cooling causes vasoconstriction facilitating platelet aggregation and fibrin formation. In an embodiment, a neural blockade agent, an anesthetic agent, an analgesic agent, a vasoconstriction agent, a sclerosant agent, or any combination thereof, may be applied to stabilize the injured and breached vessels to allow platelet aggregation and fibrin formation and to allow a fibrin clot to become stable to sustain hemostasis.

The coolant may be a liquid, it may be a solid, a sludge, or a gel. The coolant may change phases, for example, melting from solid to liquid, during application. As an example, the coolant is water. Alternatively, the coolant water may contain at least one electrolyte, for example, calcium chloride or ammonium nitrate. In another embodiment, the coolant is water containing a water-soluble or a water-dispersible polymer, such as, for example, sodium carboxymethyl cellulose, cellulose ether, guar gum, sodium polyacrylate, polysaccharide, and the like. The initial coolant can be refrigerated or frozen prior to use. The coolant can be activated by an electrical force in some embodiments.

In one aspect of the invention, the coolant is selected from a class of Phase Change Material (PCM) capable of maintaining a narrow melting temperature range at the selected temperature range. The PCM is capable of absorbing or releasing relatively large amounts of latent heat at a relatively constant temperature, typically referring to melting from solid to liquid or solidifying from liquid to solid. In an embodiment, the PCM is a salt hydrates. The coolant may be a bio-based fat, fatty acid, ester, oil, or the like. Alternatively, the coolant may be a petroleum-based hydrocarbon, synthetic alkane, ester, mineral oil, paraffin, other organic derivative, and the like. By way of example, the melting temperature of the PCM is selected to be between about −15° C. and about +25° C. A PCM material can be used singularly or in combination with another PCM material.

In one aspect of the invention, the volume of the coolant is dependent on the nature of the injury, the therapy surface area, and the duration of the therapy. The volume of the coolant to the affected breached skin site can be between about 3 cm$^3$ and about 500 cm$^3$. The coolant can deliver and transfer cooling to the wound site in a passive manner. Alternatively, the coolant can be controlled by an active refrigerative instrument such as a battery or AC-powered cooling instrument and delivers and transports cooling to the breached injured skin for a desired duration. An electronic control can electronically control and administer the cooling temperature to the wound site for a predetermined duration according to the wound healing phases.

In one embodiment of the invention, the initial temperature of the coolant upon application to a patient is provided by an active means, for example, an electrical refrigerative force. Alternatively, the initial temperature of the coolant upon application to a patient is provided by refrigerating the device or the CCC in a refrigerator or a freezer prior to use.

BRIEF DESCRIPTION OF THE DRAWING

The accompanying drawings, which are incorporated herein and form part of the specification, illustrate various embodiments of the present invention and together with the description, further serve to explain the principles of the invention and to enable a person skilled in the pertinent art to make and use the invention. In the drawings, like reference numbers indicate identical or functionally similar elements. A more complete appreciation of the invention and many of the attendant advantages thereof will be readily obtained as the same becomes better understood by reference to the following detailed description when considered in connection with the accompanying drawings, wherein:

FIG. 3A is the front view of an exemplary embodiment of an LSG wrapped around the surrounding anatomical structures of the injury site after the transfemoral percutaneous intervention;

FIG. 3B is an alternative front view embodiment of the LSG for the transfemoral intervention;

BEST MODE FOR CARRYING OUT THE INVENTION

Figure 1:
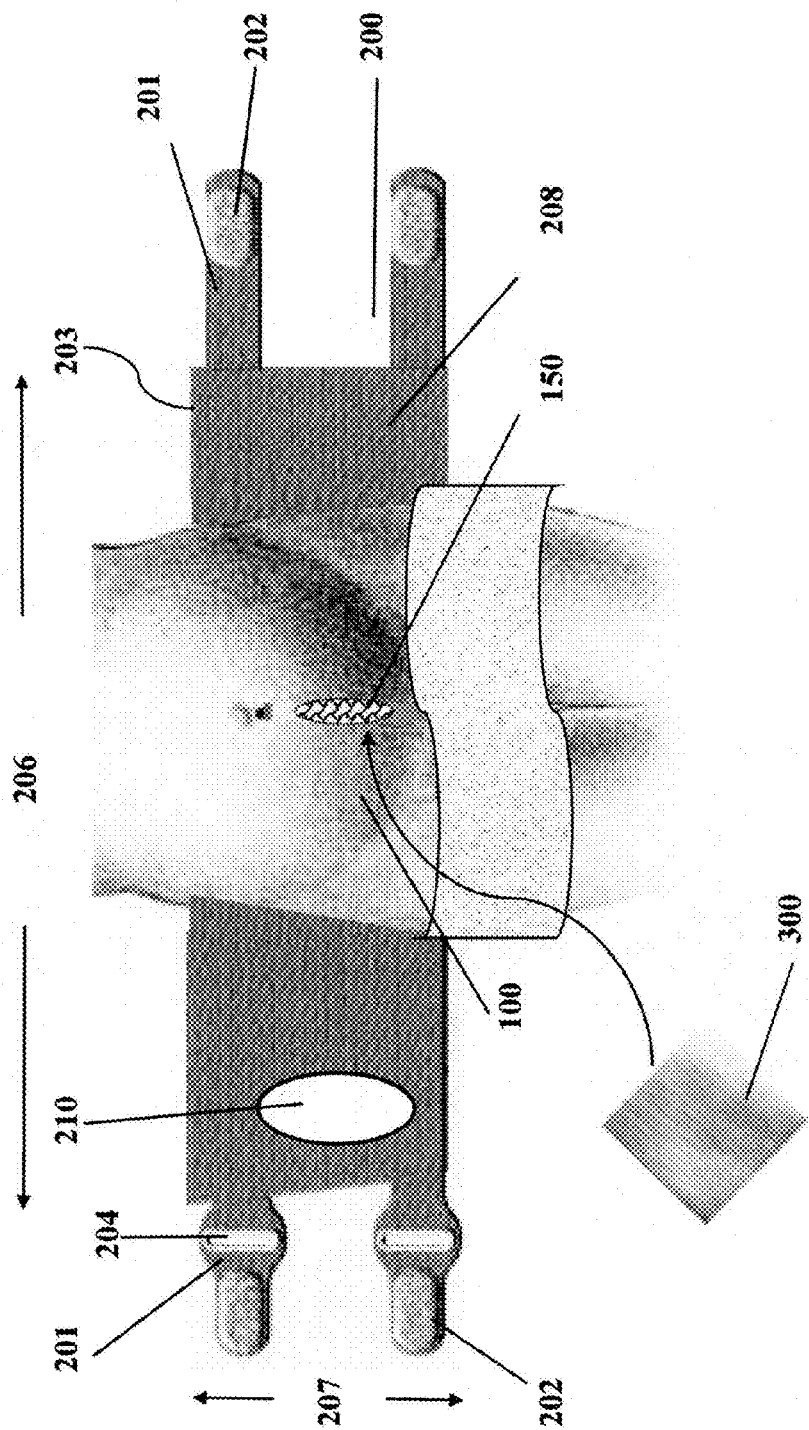
FIG. 1 is the front view of an exemplary embodiment of a lateral stabilization garment (LSG) placed under a patient prior to a surgical procedure.

In the following detailed description, reference is made to the accompanying drawings which form a part hereof and in which is shown by way of illustration specific embodiments in which the invention may be practiced. These embodiments are described in sufficient detail to enable those skilled in the art to practice the invention, and it is to be understood that other embodiments may be utilized and that structural or logical changes may be made without departing from the scope of the present invention. The following detailed description is, therefore, not to be taken in a limiting sense, and the scope of the present invention is defined by the appended claims.

In the past, intervention of a cardiovascular disease or the design of a vascular device has treated the diseased vascular segment as a rigid and stationary structure with constant dimensions. As such, precision fitting and precision deployment to the diseased vascular segment become the paramount, and sometimes the only, concern. However, ample clinical experiences and a large amount of population-based statistics have shown that these interventional devices often fail for unknown reasons and in many cases, medical complications remain unabated for decades. These clinical observations are particularly true for the bleeding and vascular complications in percutaneous femoral access interventions.

Because the injured vessel is dynamic and elastic, as a result, no amount of precision deployment and precision fitting, as currently practiced, to "anchor, plug, or seal" a vascular wound is sufficient to ensure patient safety and procedural success. The lack of real progress in percutaneous hemostasis is supported by many well-known and troublesome clinical observations including the unpredictable and unexplained delayed breach of hemostasis. Bleeding and vascular complications in these situations are often medical emergencies, not only undermining the patient's safety, but also becoming a significant societal economic burden.

This concept is the first to recognize that these seemingly subtle vasculature motions and the elastic nature of the injured vessel have a particular effect on the clinical outcomes of hemostasis and wound healing in a percutaneous intervention or in a surgical wound, and this invention suggest means to solve the identified problems. Even though this concept focuses on the design and methods of use of a topical device applied outside-of-the-body over the breached skin surface, this concept recognizes that the wound is on the vasculature (often a major artery or a major vein) under the skin, and the topical device of the apparatus is designed to affect and heal the injured vessel under the skin.

Embodiments of this invention teach how to affect and control vasculature motions and other motions in muscular/skeletal structures surrounding the injury site, particularly during the critical initial phase of platelet aggregation and fibrin clot formation. Wound healing, including initial hemostasis, is identified to consist of several distinct phases and each has its own specific time-dependent cellular activities. Without successful completion of initial cellular steps, follow-on wound healing phases are likely to be compromised. But once these initial cellular steps are completed without disruption and without agitation, the follow-on wound healing phases become a manageable process and a natural progression of the initial hemostasis success.

Definitions

By "hemostasis phase" is meant a visual determination that no blood is flowing or oozing out on the skin surface and that sufficient time has elapsed to allow a fibrin clot to become stable to minimize rebleeding.

By "wound healing phase" is meant any phase or related phases in the wound healing process including vasculature motions, hemostasis, blood coagulation, platelet aggregation, fibrin formation, re-epithelialization, inflammation, scar formation, proliferation, remodeling, and maturation, or the like.

By "vasculature motions" or "vascular motions" is meant any motions associated with the vascular system and with the local vascular segment including vasomotion, vasoconstriction, vasodilation, vasospasm, and the like.

By "wound site" or "injury site" is meant the vascular wound and the skin wound together. Even though the device is applied topically on the skin and outside of the body, the device is meant to affect the vessel wound under the skin.

By "anatomical structure" or "anatomical vicinity" or "vicinity structure" is meant the immediate vascular and musculoskeletal structures surrounding the injury site. The extent of "vicinity" is dependent on factors such as the location and the nature of the intervention.

By "coolant" is meant a material that is kept at a low temperature, as specified herein, and typically lower than the body temperature or lower than the healthy skin temperature prior to the application to a wound site. The coolant's low temperature may be maintained by an active means, such as an electrical force. Alternative, the coolant may be placed in a refrigerator or a freezer to attain low temperature prior to use. The coolant, during use, gradually heats up by absorbing heat from the injury site and from the affected areas to finally reach the ambient temperature or the body temperature of a patient. The coolant functions to keep the affected injury area at a lower temperature than the healthy skin temperature.

By "Phase Changing Material (PCM)" is meant a material that melts or solidifies within a narrow temperature range and is capable of storing and releasing large amounts of energy upon phase change.

DESCRIPTION OF THE DEVICE

Embodiments of the present invention provides means to affect and control vasculature motions during the critical phase of platelet aggregation and fibrin formation upon sheath removal or upon surgery completion, to cause hemostasis, blood coagulation, platelet aggregation and fibrin formation, leading to maintaining and sustaining hemostasis. It further promotes re-epithelialization, reduces pain, swelling, inflammation and scar formation on a patient. This device and related methods accelerate and improve overall wound healing quality.

With reference now to the drawing, FIG. 1 is graphical representation of the front view of a lateral stabilization garment (LSG) 200 placed under a patient prior to a surgical procedure. An unbroken skin 100 can have a breached injured skin wound 150. The LSG has a continuous portion 208 which has a width 206, a height 207, and a plurality of extensions 201 having securing mechanisms 202. The width is such that it covers the circumference of the anatomical structure under treatment, or slightly larger than the circumference to allow some overlap when both ends are pulled together after the medical procedure. The LSG is placed under a patient in a lying on the back position prior to medical intervention. The LSG has an opening 210 which is configured and positioned to expose the skin wound when the LSG is pulled together and wrapped around a patient after the intervention is completed. The shape of opening 210 can be a circle, a square, a rectangle, or oblong, or oval-shaped, or an irregular shape.

The LSG 200 has two, or more than two, belt-like, extensions 201 on both sides to secure the LSG over the patient after medical intervention is completed. These extensions can be a thin belt-like structure, or substantially thicker depending on the anatomical locations and the therapeutic goals. The extensions may have a hook-and-loop fastener 202 on each end, in this case represented as Velcro® in FIG. 1, and also on the backside (203), not visible from this representation. One side, or both sides, of each extension 201 has an opening 204 which allows one extension on the opposite side to be inserted through and connect to the other extension. Fastener 202 serves to secure the LSG over the patient after two extensions 201 are pulled together and wrapped around the patient. The securing mechanism can be any attachment devices including, but not limited to, a hook-and-loop fastener, an adhesive, an adhesive tape, a harness, a buckle, a clasp, a hook, a loop, a safety pin, a D-ring, or the like.

Upon securing LSG 200 over a patient, the attending medical personal may also manipulate the LSG and its components to apply mild lateral compression, for example, by pulling the extensions 201 tighter after the extensions from both sides have passed through the respective opening 204. After the LSG is secured over the patient after intervention completion, a sterilized gauze 300 or other suitable wound dressing is placed on the wound 150 in or on the LSG opening 210.

Figure 2:
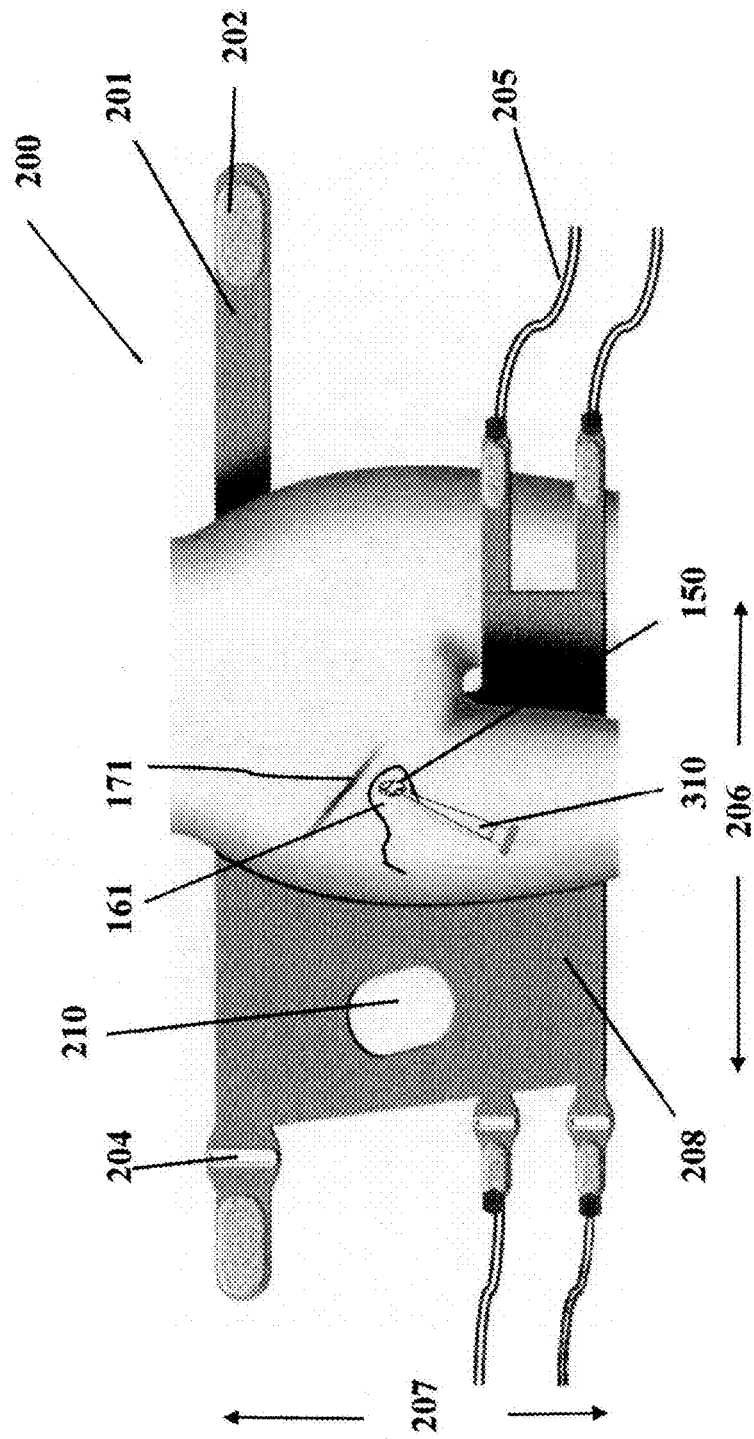
FIG. 2 is the front view of an exemplary embodiment of an LSG placed under a patient prior to transfemoral percutaneous intervention.

With reference to FIG. 2, there is shown the front view of a graphical representation of LSG 200 placed under a patient prior to transfemoral percutaneous intervention. The femoral access site injury 150 is at the femoral head 161 near the inguinal ligament with its direction indicated by 171. The intervention is shown here as completed, but the sheath 310 is still left in place ready for hemostasis management. Before the sheath is pulled, the LSG 200 is wrapped around the injury site using substantially the same mechanism described in FIG. 1. Detachable extension 205 can be a string or the like and functions as an extension to the permanent extension 201 in the LSG. In the event the circumference of the anatomical structure surrounding the injury is too small, for example, an extremity, the LSG is unlikely to spread out under the patient on both sides of the body enough to allow the attending medical personnel to easily pull both ends together and wrap it around the injury site without having to disturb the patient. The detachable extension 205 can be attached to the LSG component by a low-strength hook-and-loop fastener or the like. The detachable extension 205 allows the medical personnel to manipulate the LSG over the patient and once the LSG is secured on the patient, the detachable extension can be discarded. Embodiment FIG. 2 depicts that the upper end of the LSG is at the waistline, thus allowing the patient to sit up or tilt the upper body to release back pain and strain as the wound heals, while with minimal or no disturbance to the injury site. Embodiment FIG. 2 further depicts an opening allowing the bathroom functions by a patient as the wound heals.

FIG. 3A is an exemplary embodiment of Lateral Stabilization Garment (LSG) 250, depicted in FIG. 2 in the unwrapped configuration 200, wrapped around the injury site and the surrounding anatomical structures of the injury site after the transfemoral percutaneous intervention, and LSG 251 in FIG. 3B an alternative embodiment covering more lower torso area 220 with an overlapped flap and secured by a fastener and the like 240. Another alternative is that the LSG can also be applied to the untreated femur areas not shown in FIG. 3. FIGS. 3A and 3B are embodiments specifically for transfemoral intervention. FIG. 3 depicts that the intervention is completed, but the sheath 310 is still left on the injury site 150 ready for hemostasis management in the next step of operation. In FIG. 3, both embodiments have an opening 210 to allow the exposure of the injury site for further placement of additional therapeutic devices. In these two embodiments in FIG. 3, both have pre-fabricated back-side fasteners 203 to secure additional component such as the Cooling Pad (CP) to the LSG's 250 or 251. The mechanism to secure the CP to the LSG can be a hook-and-loop fastener, an adhesive, an adhesive tape, a harness, a buckle, a clasp, a hook, a loop, a safety pin, a D-ring, or the like. In the two embodiments of FIG. 3, both are designed not only to perform the aforementioned functions in hemostasis wound healing, but to also allow a patient to tilt up the upper body to release strain and back pain, and without causing movements to the injury site and its surrounding musculoskeletal structures. The design further allows a patient to perform bathroom functions as hemostasis wound healing progresses.

There can be various mechanisms by which two ends of the LSG can be secured together to form, for example, LSGs 250 or 251. In FIG. 3A, the securing mechanism is two belt-like structures crossing each other through an opening such as 204 as depicted in FIGS. 1 and 2, while FIG. 3B an alternative mechanism by closing one flap over the other using a fastener or the like. The embodiment of FIG. 3B provides more coverage on the front abdomen 220. Alternatively, the LSG 200 can also provide stabilization on the uninjured femur not shown in FIG. 3.

The LSG 200 can be made of a transparent polymer to provide visibility for the medical personnel and the patient to inspect the wound and the vicinity of the wound. The LSG can be made of woven or non-woven fabric. The polymeric materials for the LSG are stretchable and the degree of stretch is between about 5% in linear width direction (from 100% to 105% in width) to about 500% (from 100% to 5 times). The fabric materials for the LSG can be natural materials including, but not limited to, cotton, wool, silk, or synthetic polymeric materials, in various kinds of weave patterns. The polymeric materials can be selected from a variety of classes including, without limitation, polyester, nylon, polyacrylamide, polycrylonitrile-polyacrylamide, polycarbonate, polystyrene, low-density polyethylene, high density polyethylene, polypropylene, polyurethane, polyvinylchloride, polyvinyl alcohol, ABS, neoprene, nylon, polyethylene terephthalate, polyethylene glycol, poly-vinyl-pyrrolidone and methacrylates, ethylene vinyl acetate, polytetrafluoroethylene, expanded polytetrafluoroethylene, fluorinated polymer, fluorinated elastomer, polyolefin, silicon-containing polymer, polysilicone, a mixture of the aforementioned, or the like.

Figures 4, 4A, 4B:
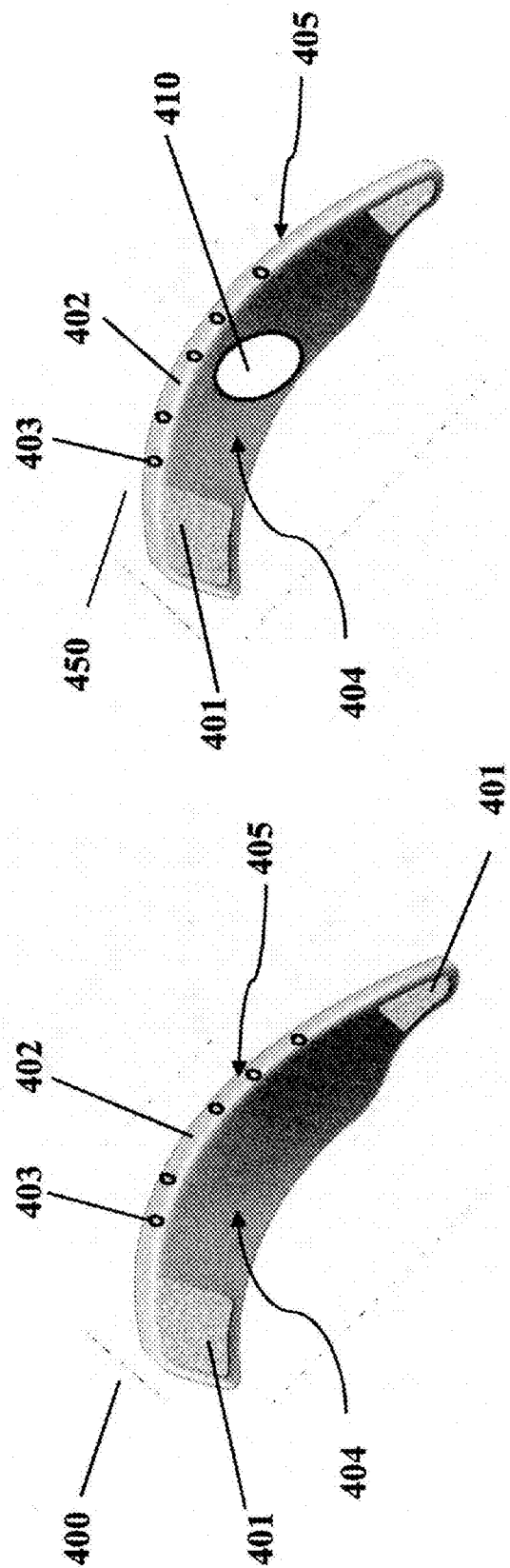
FIG. 4A is the side view of an exemplary embodiment of a cooling pad (CP) covering the opening in the LSG in FIGS. 3A and/or 3B applying cooling and compression.
FIG. 4B is the side view of an alternative exemplary embodiment of a CP exposing the injury site while covering the opening in the LSG in FIGS. 3A and/or 3B.

FIG. 4A is a Cooling Pad (CP) 400 covering the opening 210 of the LSG in FIGS. 3A and 3B to apply cooling and compression to the injury site. FIG. 4B is another exemplary embodiment of a CP 450 having an opening 410 allowing the exposure of the injury site for further placement of additional therapeutic devices. Both embodiments of FIG. 4 are configured to be placed on top of the LSGs 250 and 251 for the transfemoral hemostasis applications depicted in FIG. 3 and secured to LSG by fastener 401. The CP 400 and 450 in FIG. 4 further comprise a secure strap fastener mechanism to secure CP 400 or 450 to the LSG in FIG. 3. The securing mechanism to the LSG can be a hook-and-loop fastener, an adhesive, an adhesive tape, a harness, a buckle, a clasp, a hook, a loop, a safety pin, a D-ring, or the like, or the combination of more than one mechanism.

The CPs in FIG. 4 further comprise a volume indicated by a depth 402 of the device. The volume contains coolant 403 which provides cooling to the injury site and the surrounding anatomical structures. The thicker the depth 402, the greater the amount of the coolant that a CP can contain. In FIG. 4, both CPs are configured to conform to the anatomical structure of the injury site and its anatomical vicinity, and also to the LSG to which the CP adheres. In FIG. 4, both CPs have two surfaces, the inner surface 404 and the outer surface 405 (which is invisible here). The inner surface 404 is the surface that faces the injury site and the outer surface 405 is exposed to ambient air.

The CP 400 delivers and transports cooling to the injury site, or to the injury and its anatomical vicinity. CP 400 may comprise one cooling zone or a plurality of cooling zones, each have the same or a different temperature. For example, the first zone may be at the center portion of the CP and the second zone outside of the first zone covering the outside portion of the CP. The temperature zones can take a variety of shapes and sizes corresponding to medical needs, such as, for example, substantially circular, substantially square, substantially rectangular, polygon, or the like. The temperature of each zone can be altered according to the temperature of other zones. The temperature of each zone can also be altered independent of the other zones.

The embodiments of CPs 400 and 450 in FIG. 4 can comprise a transparent polymeric material allowing the attending medical personnel or the patient to visually inspect the wound site. The embodiments of the CPs in FIG. 4 can comprises one type of polymeric material, or the combination of more than two types of polymeric material. Preferably, the inner surface 404 is made of thermal conductive materials to affect heat removal from the injury site. Alternatively, the inner surface of CPs is made of soft fabric material, such as, without limitation, terry cloth fabric or gauze type of materials, whereas the material possesses the required characteristics of conformance and certain thermal conductivity to provide therapy and improve patient's comfort. The inner surface 404 can be in direct contact with the injured skin and the surrounding area of intact skin. Alternatively, the injured skin can be covered with a sterilized gauze or other wound dressing and the inner surface is then placed over the sterilized gauze or a wound dressing. Preferably, the outer surface 405 of the CPs is made of a thermal insulation polymer, such as, without limitation, neoprene, silicone, polyurethane, or the like.

After the transfemoral percutaneous procedure is completed, and while the sheath is still on the access site, the attending medical personnel first completes the placement of the LSG 200 in FIG. 2 into position as depicted in the LSGs in FIG. 3. In the event a Vascular Closure Device (VCD) implant is deployed to the arterial "hole" to stop bleeding, the sheath is no longer in place at this point. Without a sheath in place (implant hemostasis), the attending medical personnel then places CP 400 over the opening 210 (FIG. 3A or 3B) and completes the hemostasis procedure and releases the patient to rest with follow up schedules by nursing staff per hospital protocol. In the event the sheath is still in place at this point, CP 450 in FIG. 3B is placed over the sheath keeping the sheath undisturbed inside the opening 410.

Figure 5:
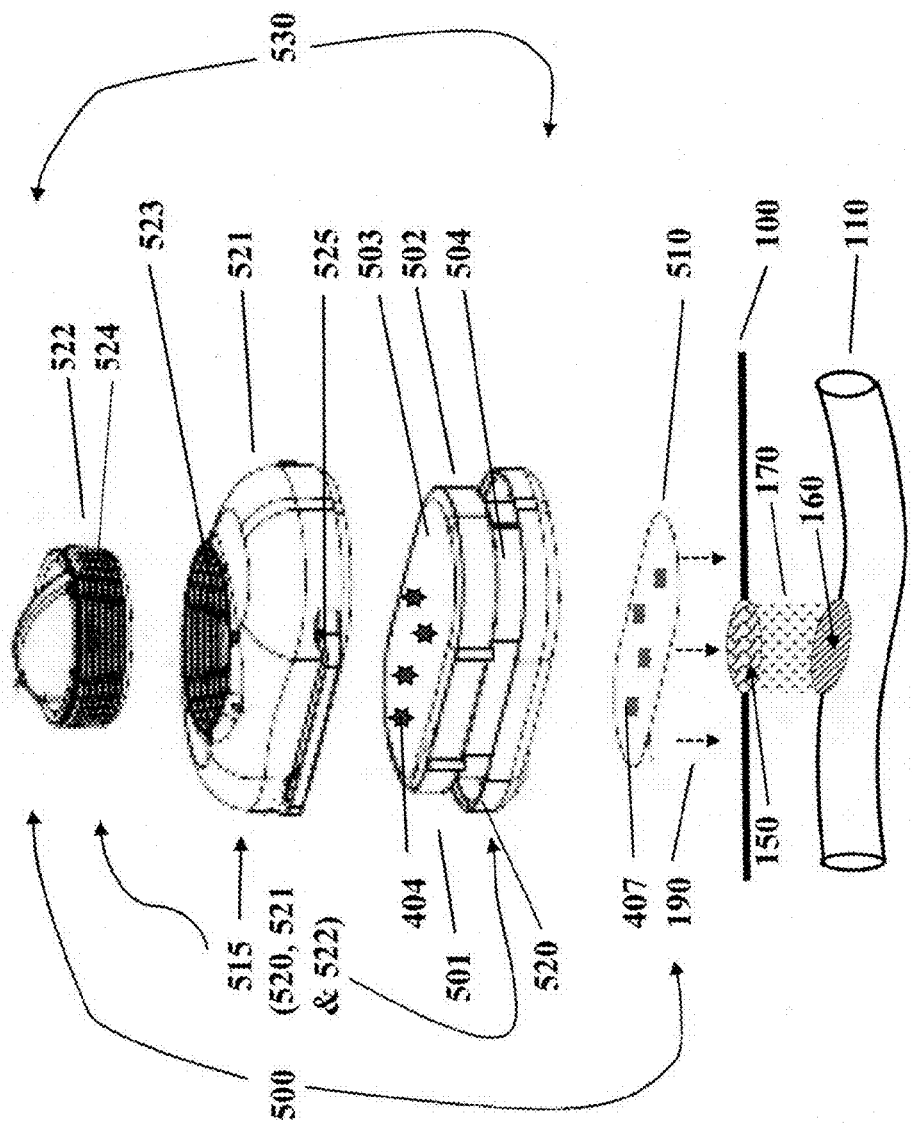
FIG. 5 is the exploded view of an exemplary embodiment of the cooling compressive device (CCD) and its components.

FIG. 5 shows an exploded view of an exemplary embodiment of the Cooling Compressive Device (CCD) 500. The CCD further comprises a Cooling Compressive Compartment (CCC) 530 and a Cooling Compressive Surface (CCS) 510. The CCD is placed over the skin injury site 150 and its anatomical vicinity of unbroken skin surface 100. Under the skin surface, the vessel 110 has a vessel injury 160 and the tissue injury 170 connecting the skin injury 150 and the vessel injury 160. The CCD 500 can be placed directly over the skin injury 150. Alternatively, the skin injury 150 can be covered with a sterilized gauze or a wound dressing or the like first before placing the CCD over the wound dressing.

The CCS 510 delivers and transports a compressive pressure 190 to the wounds 150, 160, and 170 and its anatomical vicinity. The CCS further delivers and transports cooling from coolant 404 contained inside the coolant container reservoir 502 which is covered with cap 503, to the injuries 150, 160, and 170 and its surrounding anatomical structures and in the direction of depicted by arrows 190. The CCS may incorporate a pharmaceutical agent 407 which is delivered and transported to the injuries 150, 160, and 170 and its anatomical vicinity. The CCS 510 may provide uniform cooling to the injury site. Alternatively, the CCS may comprise more than one cooling zone having different temperatures in different zones. For example, the first zone may be at the center portion of the CCS and the second zone outside of the zone covering the outside portion of the CCS. The temperature zones can take a variety of shapes and sizes corresponding to the use, for example, without limitation, substantially circular, substantially square, substantially rectangular, polygon, or the like. The temperature of each zone can be altered according to the temperature of other zones, or they can also be altered independent of the other zones, depending on use requirements. Alternatively, the plurality of zones is selected according to the nature of the wound and the anatomical location of the wound.

In one embodiment, the CCS 510 comprises both rigid and elastic characteristics and may comprise one polymeric material or a combination of two or more than two polymeric material. One, or at least one, polymeric material has the rigidity to resist outward blood flow. In one embodiment, one, or at least one, polymeric material, is thermally conductive with a thermal conductivity of between about 0.15 W/(m-K) and about 100 W/(m-K). The polymeric material can be an elastomer possessing viscoelastic property and can be selected from a variety of classes such as polyurethane, silicone, neoprene, or other specialty or proprietary materials such as a thermal-conductive silicone or a thermal-conductive polymer, such as, for example, CoolPoly®. In one embodiment, one, or at least one polymeric material is soft, flexible, and elastic with a tensile modulus from about 50 kPa to about 100 MPa, to impart comfort and therapeutic effect to a patient. As a reference, typical human skin has a tensile strength of approximately 20 MPa and typical human vessels have the tensile strength of between 50 kPa and 3.0 MPa.

The CCC can have a coolant container 501 containing coolant 404. The coolant container is depicted in FIG. 5 with a reservoir 502 and a cap 503. In one embodiment, the CCC further comprises a vertical displacement casing 515 consisting of a ring 520, a housing 521, and a presser 522. Prior to operation, the presser thread 524 is already engaged in the presser cavity 523 and the bottom part of housing 521 is already mated with the upper part of ring 520 and becoming one unit. During operation, the operator adjusts the presser 522 and the movement of the presser thread affects the up-and-down movement of the coolant container 501, causing vertical displacement. In this operation, the part lower portion 504 of the reservoir 502 protrudes out of the ring 520 and comes in contact with the injury site. The total vertical displacement of the coolant container is between about 0.2 mm and about 10.0 cm, with the extreme high level of vertical displacement being employed for an obese patient in femoral access site application. The greater the vertical displacement, the greater the compressive pressure.

In one embodiment, the presser 522 has a presser thread 524 with a height. The presser height corresponds to the height of the lower portion 504 of the coolant reservoir 502 and together determines the amount of total vertical displacement. The adjustment of the presser 522, for example, can be accomplished by turning the thread in the presser clockwise or counterclockwise, thus either pushing down or raises the coolant container 501 relative to the injury site. The up-and-down vertical displacement can alternatively be caused by other similar mechanisms such as a hydraulic pump. The down vertical displacement of coolant container 501 provides a compressive pressure to the injury, and the up vertical displacement releases the compressive pressure from the injury site. In one embodiment, the CCD 500 comprises a handle 525 to allow engaging the CCD 500 to CP 400 or to LSG 250 or 251, or to both the CP and the LSG. The securing or engagement mechanism can be a handle, a hook-and-loop fastener, an adhesive, an adhesive tape, a harness, a buckle, a clasp, a hook, a loop, a safety pin, a D-ring, or the like, or any combination thereof.

The CCC 530 can be made of a metallic material or an alloy. The metallic material can be an elemental metal and a metal alloy selected from a variety of classes such as steel, copper, brass, titanium, titanium alloy, aluminum, iron, and the like. Alternatively, the CCC 530 can be made of a polymeric material, or a combination of two or more polymeric materials. The polymeric material can be a plastic, a composite, a compounded material, a blend, a high-durometer elastomer, or any combination thereof. The polymer can be selected from a variety of classes including, polycarbonate, polystyrene, low-density polyethylene, high density polyethylene, polypropylene, polyurethane, polyvinylchloride, polyvinyl alcohol, ABS, neoprene, nylon, polyethylene terephthalate, polyethylene glycol, poly-vinyl-pyrrolidone and methacrylates, ethylene vinyl acetate, polytetrafluoroethylene, expanded polytetrafluoroethylene, fluorinated polymer, fluorinated elastomer, polyolefin, silicon-containing polymer, polyacrylamide, polycrylonitrile-polyacrylamide, polyester, polysilicone, a mixture of the aforementioned biocompatible materials, or the like.

The polymeric materials in CCC 530 can be transparent or translucent to provide visibility to the attending medical personnel and to the patient to inspect the wound site without disturbing the wound site or the device. The polymeric materials in the CCC are so configured and selected so that the CCC side facing the CCS 510 is more thermally conductive to providing cooling therapy to the patient, while all other sides have good thermal insulation to prevent coolant from losing cooling capability to the ambient.

To use the CCD 500 in transfemoral application, a patient will be prepared and in position as depicted in FIG. 3A or 3B after medical intervention is completed. In other words, the LSG is fully secured in place and the sheath is still in place. At this time, the attending medical personnel secures the CP 450 in FIG. 4B to the LSGs in FIG. 3, still leaving the sheath undisturbed at the access site in opening 410. The medical personnel then uses one hand to place CCD at the injury site, and with hand pressure to press the CCD against the injury site while using the other hand to pull the sheath. This step of operation is similar to the application of the current topical clamp-type compression device. Once the sheath is pulled, the medical personnel continues to use one hand to hold down the CCD 500 while using the other hand to turn the presser 522 until there is no active bleeding or oozing. This step of operation is also similar to the current topical clamp-type compression device. Once active bleeding is under control, the medical personnel may make fine-adjustment until the CCD is properly engaged.

The vertical displacement of the CCD 500 in this invention imparts only a force in a substantially vertical direction to the injury site and its anatomical vicinity, without imparting forces in another manner such as pulling or twisting the injury site to cause further injury to the wound. The vertical displacement can be finely tuned to as small an increment as possible, that is, as small as about 0.05 mm, to accommodate a particular medical need for a particular injury, a particular anatomy, or a particular intervention. The adjustment of vertical displacement, and thereby the adjustment of the compressive pressure, can be done in a precise, reversible, and incremental manner, without any perturbation to the patient or to the wound, thus minimizing irritation or agitation to the wound to sustain hemostasis and promote wound healing.

Figure 6:
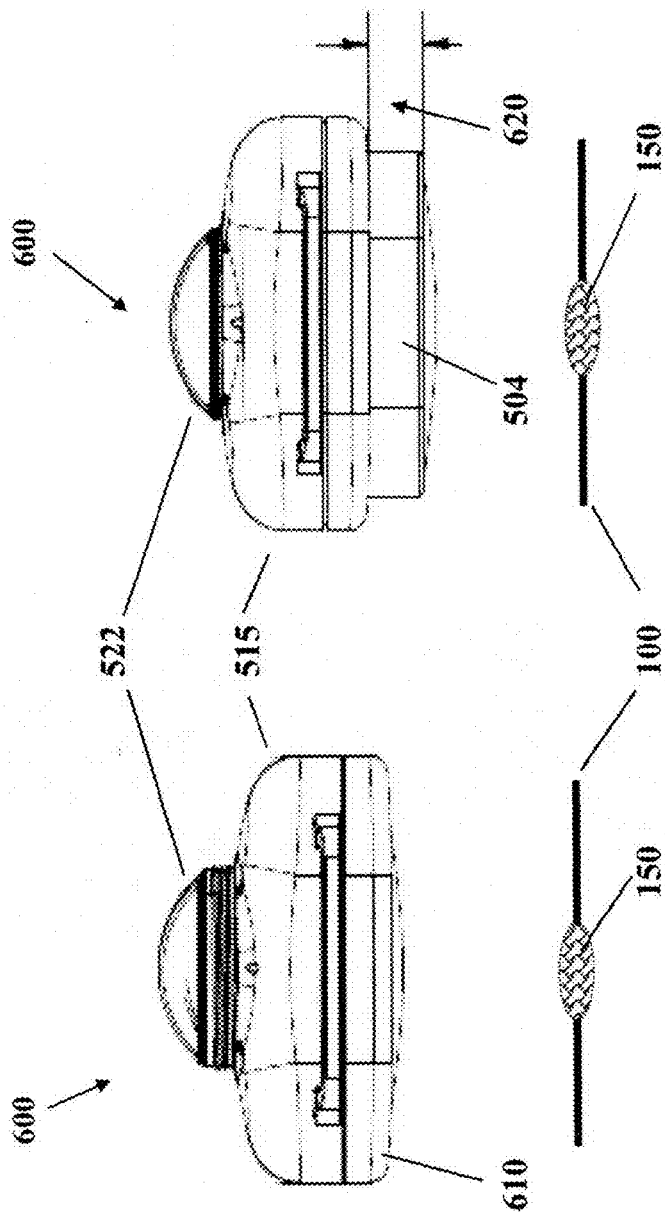
FIG. 6A is a side view of an exemplary embodiment of the CCD as applied to a wound site upon completion of a surgical procedure or a percutaneous intervention prior to application.
FIG. 6B is a side view of an exemplary embodiment of the CCD in use where the coolant container is vertically depressed from the original configuration relative to the pre-application position in FIG. 6A.

With reference to the embodiment of FIGS. 6A and 6B, side views of a CCD 500 are shown in a fully assembled state 600 in preparation for application (FIG. 6A) and during application (FIG. 6B) for transfemoral percutaneous intervention. In FIG. 6A, the presser 522 in a form of a thread screw in the vertical displacement casing 515 is in the raised and resting pre-application position and not visible in this depiction. In FIG. 6B, the presser 522 is fully turned down and depressed and the lower portion 504 of the coolant reservoir 502 (FIG. 5) is lowered by a certain vertical displacement 620 and visible in this side view. Notice that the coolant reservoir is depressed and displaced from the original configuration relative to and independent of the casing 515. In both FIGS. 6A and 6B, the cooling compressive surface 510 is not visible. Upon hemostasis and wound healing, the presser 522 can be turned up in a gradual and precise manner to release compressive pressure at the injury site.

Figure 7:
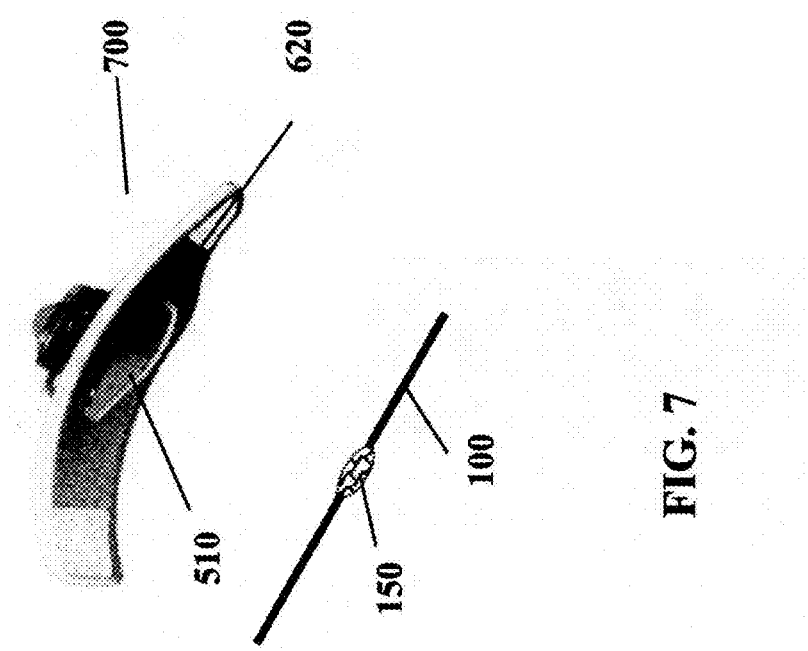
FIG. 7 is the tilted side view of an exemplary embodiment of the CCD engaged to CP for application of cooling and compression.

With reference to FIG. 7, this is the slanted tilted side view of an exemplary embodiment of CP and CCD assembled together 700 and depicted over the unbroken skin 100 and skin injury 150. The CCS 510 is the outmost layer facing the wound and depicted in this embodiment as having a slight ridge in the center. In this configuration, the coolant container is lowered from the CP by the amount indicated by 620 representing device in use and performing compression.

Figure 8:
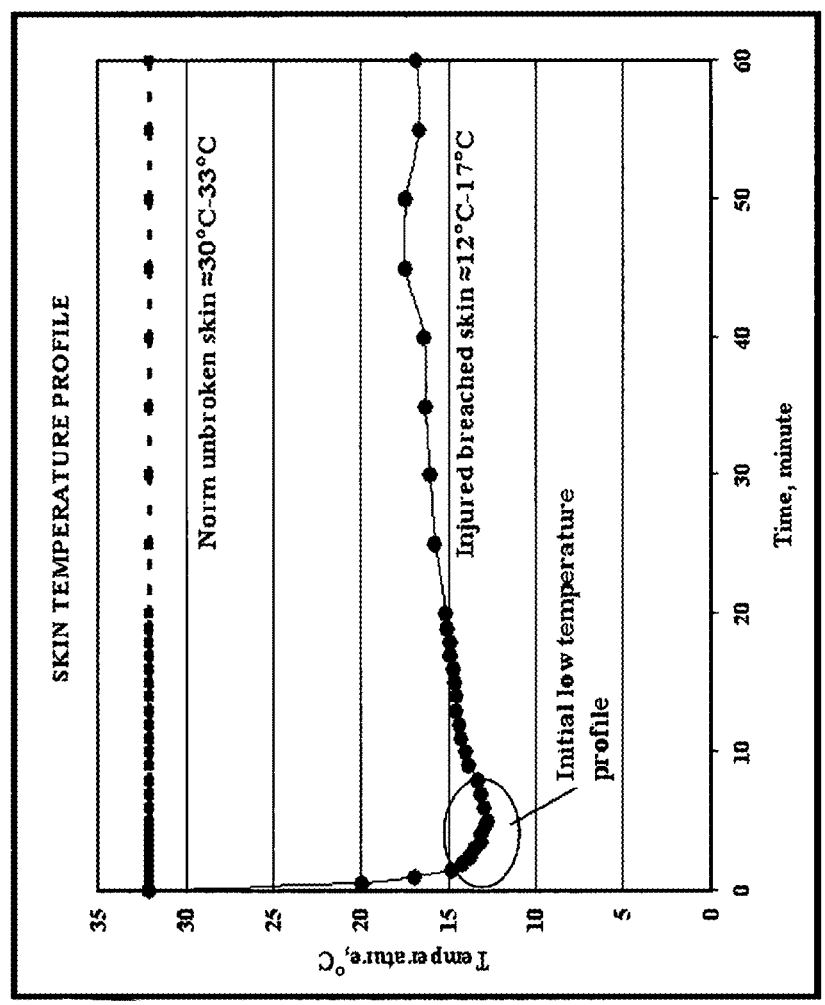
FIG. 8 is an exemplary embodiment of a skin temperature profile as a function of time upon the application of the CP or upon the application of the CCD, or both.

With reference to FIG. 8, there is shown a representative skin temperature profile as a function of time upon the application of the Cooling Pad (CP) 400 or upon the application of the Cooling Compressive Device (CCD) 500, or both. The surface temperature of the unbroken skin in a body may vary depending on many factors including anatomical location, the health/disease state of a patient or the ambient conditions, but it is generally within the range between about 30.degree. C. and about 33.degree. C. During the application of the present device, the skin temperature (injury site and its anatomical vicinity) has an initial temperature dip for a certain duration which is followed by a substantially constant temperature for another duration. Typically, the initial injury skin temperature dip is between +5.degree. C. and +20.degree. C. for the duration up to ten minutes. The initial low temperature dip is such that a patient in the conscious state does not feel too cold and request that the device be removed. After the initial temperature dip, the skin temperature starts to rise and attains an equilibrium within a substantially constant temperature range which is comfortable and tolerated by patient. The follow-on cooling temperature and its duration depend on the type of injury and the condition of the patient, either in a sedated or in a conscious state. A typical temperature in the follow-on phase is between about +10.degree. C. and about +25.degree. C. for a duration of between five minutes and 20 hours. The follow-on duration may also depend on hospital protocol in keeping patient under observation or treatment. In case of medical need, a new device may replace a prior device after the prior device has reached the ambient temperature. The total length of time that the device is applied to a patient can typically be 24 hours or less for an overnight in-patient. Depending on the hospital protocol and the medical need of the patient, the device can also be applied on a patient for a longer period of time.

Figure 9:
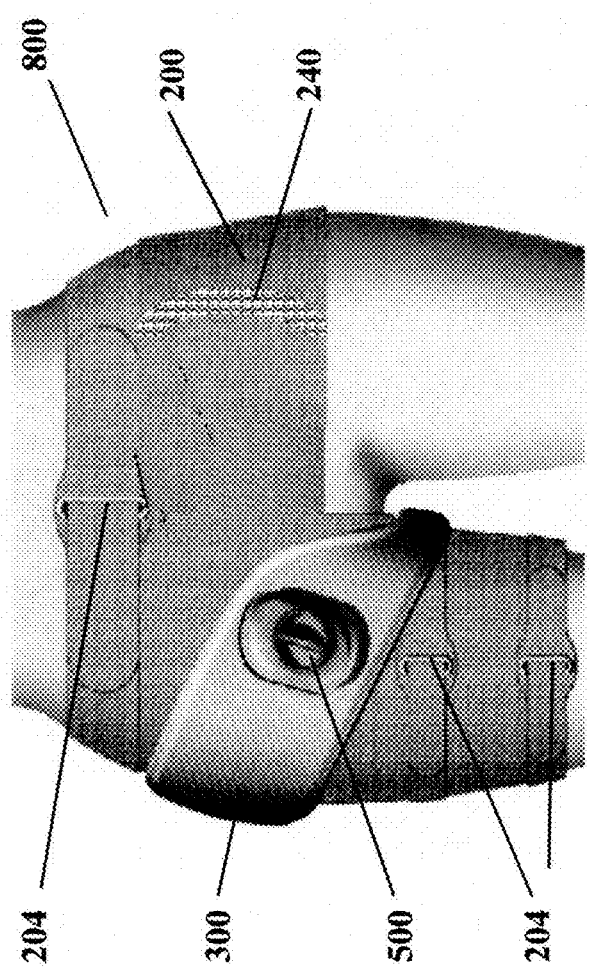
FIG. 9 is a front view of an exemplary embodiment of a hemostasis wound healing device (HWHD) comprising a LSG, a CP and a CCD as applied to heal the percutaneous transfemoral access site wound.

With reference now to FIG. 9, there is shown a hemostasis wound healing device (HWHD) 800 comprising a Lateral Stabilization Garment (LSG) 200, a Cooling Pad (CP) 400, and a Compressive Cooling Device (CCD) 500 in application for healing the percutaneous femoral access site wound. The exemplary device HWHD 800 in FIG. 9 is secured by two different mechanisms, one is with a hook-and-loop fastener and a rectangle-shaped ring 204 and one with such a fastener or other types of fabric adhesives 240. There are numerous variations, changes, and substitutions to the above two mechanisms to secure two ends of fabric together to allow lateral stabilization and mild compression to be possible, and those skilled in the art would be aware that such embodiments are provided by way of example only.

The delivery and transport of compressive pressure 190 in FIG. 5, pharmaceutical agent 407 in FIG. 5, coolant 403 in FIG. 4, and coolant 404 in FIG. 5 to the injury site and its anatomical vicinity can be by a passive diffusive means, or by an active means such as by applying an electrical source. The compressive pressure 190, coolants 403 and 404, and pharmaceutical agent 407 can individually, or together, affect the wound and promote hemostasis and wound healing. The surface area of the CCS 510 can be identical to the surface area of the injury site 150, or up to 1,000 times larger than the surface area of the skin wound. A larger surface area of the CCS is to provide therapy to heal the surrounding vasculature and tissue structures. The wound 150 can be at the center of the CCS 510, or off the center of the CCS 510, depending on the goal of the therapy.

The pharmaceutical agent 407 can be any agent that affects and controls vasculature motions in the hemostasis phase and in the wound healing phases, and promote all wound healing phases and related phases. The therapeutic agent is selected from the group consisting of cellular proliferation inhibitor, smooth muscle inhibitor, inhibitor of vascular cell growth, anti-proliferative agent, neural blockade agent, anti-inflammatory agent, antibiotic, anesthetic agent, analgesic agent, pain killing agent, neuroprotectant, vasoconstriction agent, sclerosant agent, gene, DNA, RNA, polypeptide, protein, blood coagulation agent, platelet agent, blood-clotting agent, hemostasis agent, wound healing agent, and any combination thereof.

Temperature generated by the coolant is to lower the temperature at the breached skin surface of the injury site and lower the temperature of the anatomical vicinity of the injury site. In one embodiment, the temperature profile reflects a temperature that alters as a function of time corresponding to the wound healing phases. In one embodiment, the temperature profile corresponds to the temperature requirement of each hemostasis phase and wound healing phase in the wound healing process, and corresponds to the time requirement of each hemostasis phase and wound healing phase. Alternatively, the temperature profile corresponds to the temperature requirement of a single wound healing phase of the wound healing process.

The coolant, for example, coolant 403 in CP 400 and in CP 450, and coolant 404 in CCC 530, can be a liquid or a solid. The coolant can be placed onto the reservoir directly or placed inside of a thin film membrane first, similar to a water balloon, before placing the coolant-in-thin-film into the reservoir 502. Cooling by the coolant can be prepared by refrigerating or by freezing the coolant prior to application. Cooling can also be generated by an external power, such as a battery or AC-powered cooling instrument and delivered and transported to the wound site. The coolant can be pure water or water containing at least one electrolyte, for example, calcium chloride, or ammonium nitrate, and the like. The coolant can also be water containing a water-soluble or a water-dispersible polymer or a mixture of such polymers, for example, sodium carboxymethyl cellulose, cellulose ether, guar gum, sodium polyacrylate, polysaccharide, and the like.

The coolant can also be selected from a class of Phase Change Material (PCM) capable of maintaining a narrow melting temperature range at a selected temperature range. The cooling material can be a bio-based fat, fatty acid, ester, or oil, and the like. The cooling material can also be a petroleum-based synthetic alkane, ester, paraffin, mineral oil, or other organic derivative, and the like. The cooling materials can be used singularly or in combination, depending on application needs. When using PCM as a coolant for this application, the melting temperature selected is between about −15° C. and about +25° C. Prior to application, the temperature of coolant can be maintained in a cooler, such as a refrigerator or a freezer.

The temperature at the breached skin surface and the coolant temperature are related to each other by a variety of factors such as the amount (volume) and the nature (specific heat, or latent heat) of the coolant, the design parameters of the device, the material selection of the cooling compressive surface CCS, the design parameters and the material selection of the coolant compartment, and the like. The design parameters and the material selections are such that the temperature on the skin surface does not cause redness or cold blisters upon device application and is tolerated by the patient, either in a conscious or a sedated state, while in use. One example of the temperature profile at the breached injured skin surface 150 as a function of time is shown in FIG. 9.

The foregoing has described the principles, embodiments, and modes of operation of embodiments of the present invention. However, the concept should not be construed as being limited to the particular embodiments described above, as they should be regarded as being illustrative and not as restrictive. Modifications and variations of the disclosed embodiments are possible in light of the above teachings. It is therefore to be understood that the present concept may be practiced otherwise than as specifically described herein. It should be appreciated that variations may be made in those embodiments by those skilled in the art without departing from the scope of the present invention.

While preferred embodiments of the present invention have been shown and described herein, it will be obvious to those skilled in the art that such embodiments are provided by way of example only. Numerous variations, changes, and substitutions will now occur to those skilled in the art without departing from the concept. It should be understood that various alternatives to the embodiments described herein may be employed in practicing the present concept. It is intended that the following claims define the scope of the invention and that methods and structures within the scope of these claims and their equivalents be covered thereby.

What is claimed is:

1. A topical hemostasis wound healing device configured to an elastic and dynamic nature of injured blood vessels to affect a hemostasis phase and a wound healing phase of a vascular wound or an acute surgical wound in a medical patient, the topical hemostasis wound healing device comprising:
    a lateral stabilization component and
    a cooling compressive component comprising
        a vertical displacement casing comprising
            a presser having threads;
            a housing having threads surrounding a cavity of the housing; and
            a ring mated with a bottom portion of the housing;
        a coolant container;
    wherein the cavity of the housing is configured to receive a bottom portion of the presser;
    wherein the threads of the presser engage with the threads of the housing;
    wherein a bottom surface of the presser directly contacts a top surface of the coolant container so as to control motion of the coolant container along a first direction perpendicular to a bottom surface of the coolant container;

wherein said lateral stabilization component is a lateral stabilization garment configured to stabilize the vascular wound or the acute surgical wound and surrounding anatomical structure thereof, and wherein said cooling compressive component is anatomically configured to provide cooling and compression to the vascular wound or the acute surgical wound and immediate anatomical vicinity thereof to affect the vascular wound or the acute surgical wound.

2. The topical hemostasis wound healing device according to claim 1, wherein the lateral stabilization garment comprises a continuous portion and a releasable securing mechanism on both ends of the continuous portion; and wherein the continuous portion has a width and a length configured to apply lateral stabilization and mild compression to the surrounding anatomical structure of the vascular wound or the acute surgical wound.

3. The topical hemostasis wound healing device according to claim 2, wherein the continuous portion of the lateral stabilization garment is anatomically configured to prevent a patient from being in a strained and constrained position for a prolonged period of time causing medical events, and to allow the patient to perform bodily functions during a healing process of the vascular wound or the acute surgical wound, including tilting a head or an upper torso, sitting up in bed, walking, and bathroom functions.

4. The topical hemostasis wound healing device according to claim 2, wherein the releasable securing mechanism of said lateral stabilization garment comprises spaced elongated extensions each having a first end with an opening and a second end configured to allow mating of the first and second ends of each of the spaced elongated extensions during application by inserting the second end of each of the spaced elongated extensions through the opening of the first end of each of the spaced elongated extensions to apply even lateral compression pressure.

5. The topical hemostasis wound healing device according to claim 2, wherein said releasable securing mechanism comprises a hook-and-loop fastener, an adhesive, an adhesive tape, a harness, a buckle, a clasp, a hook, a loop, a safety pin, or a D-ring.

6. The topical hemostasis wound healing device according to claim 2, wherein said lateral stabilization garment is selected from a group consisting of natural or synthetic polymeric woven and non-woven stretchable materials having a degree of stretch between 5% and 500% in a width direction.

7. The topical hemostasis wound healing device according to claim 1, wherein the cooling compressive component further comprises a cooling compressive surface.

8. The topical hemostasis wound healing device according to claim 7, wherein the cooling compressive surface comprises at least one component and said at least one component has an elastic tensile modulus between 50 kPa and 100 MPa.

9. The topical hemostasis wound healing device according to claim 8, wherein said at least one component of the cooling compressive surface is a thermally conductive metallic material or a polymeric material with thermal conductivity between 0.15 W/(m-K) and 100 W/(m-K).

10. The topical hemostasis wound healing device according to claim 7, wherein said cooling compressive surface contains a pharmaceutical agent selected from the group consisting of cellular proliferation inhibitor, smooth muscle inhibitor, inhibitor of vascular cell growth, anti-proliferative agent, neural blockade agent, anti-inflammatory agent, antibiotic, anesthetic agent, analgesic agent, pain killing agent, neuroprotectant, vasoconstriction agent, sclerosant agent, gene, DNA, RNA, polypeptide, protein, blood coagulation agent, platelet agent, blood-clotting agent, hemostasis agent, and wound healing agent.

11. The topical hemostasis wound healing device according to claim 1, wherein the coolant container is in the cavity of the housing.

12. The topical hemostasis wound healing device according to claim 11, wherein the presser of said vertical displacement casing controls and affects a displacement of the coolant container in the first direction.

13. The topical hemostasis wound healing device according to claim 12, wherein the displacement of the coolant container is configured to affect a compressive pressure on the vascular wound or the acute surgical wound between 0.2 psi and 20 psi.

14. The topical hemostasis wound healing device according to claim 1, wherein the coolant container contains a coolant selected from the group consisting of water, water containing at least one electrolyte, water containing at least one polymeric material, and a phase change material.

15. The topical hemostasis wound healing device according to claim 14, wherein the phase change material has a melting temperature between −15° C. and +25° C. and is selected from the group consisting of bio-based fat, fatty acid, petroleum-based product, synthetic alkane, ester, mineral oil, and paraffin.

16. The topical hemostasis wound healing device according to claim 1,
wherein a handle is directly attached to the housing of the vertical displacement casing.

17. The topical hemostasis wound healing device according to claim 1,
wherein the coolant container moves down by turning the presser about the first direction; and
wherein the coolant container moves up by turning the presser about a second direction opposite the first direction.

18. The topical hemostasis wound healing device according to claim 1, wherein the cooling compressive component further comprises a cooling pad being a continuous structure covering the vascular wound or the acute surgical wound and the immediate anatomical vicinity thereof.

19. A method of affecting a hemostasis phase wound healing in a patient using the topical hemostasis wound healing, device of claim 1 the method comprising the steps of:
placing the lateral stabilization garment under the patient in a lying down position prior to a medical procedure, the garment being substantially centered around the vascular wound or the acute surgical wound;
bringing two ends of the lateral stabilization garment together and securing the lateral stabilization garment on the patient with a mild lateral compression pressure;
leaving the vascular wound or the acute surgical wound exposed after the medical procedure is completed;
positioning a cooling pad on an opening of the lateral stabilization garment; securing the cooling pact to the lateral stabilization garment;
applying the cooling compressive component;
turning the presser to affect the displacement of the coolant container toward the vascular wound or the acute surgical wound; and
stopping the presser from advancing further toward the vascular wound or the acute surgical wound upon visual verification of no blood oozing out from the vascular wound or the acute surgical wound.

20. The method according to claim 19 further comprising: delivering and transporting cooling temperature and a therapeutic agent from the cooling pad and the coolant container to the vascular wound or the acute surgical wound and to the immediate anatomical vicinity thereof.

21. The method according to claim 20, wherein the method produces an initial temperature of skin at or around the vascular wound or the acute surgical wound between +5° C. and +20° C. for up to 10 minutes and a follow-on temperature between +10° C. and +25° C. between five minutes to 20 hours.

* * * * *